United States Patent [19]
Wang et al.

[11] Patent Number: 5,985,432
[45] Date of Patent: *Nov. 16, 1999

[54] POROUS ABSORBENT MATERIALS HAVING MODIFIED SURFACE CHARACTERISTICS AND METHODS FOR MAKING THE SAME

[75] Inventors: Lin Wang; Ebrahim Rezai; Yumiko Hayashi, all of Cincinnati, Ohio

[73] Assignee: The Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/779,725

[22] Filed: Jan. 6, 1997

Related U.S. Application Data

[63] Continuation of application No. 08/224,454, Apr. 7, 1994, abandoned, which is a continuation-in-part of application No. 08/197,916, Feb. 17, 1994, abandoned.

[51] Int. Cl.$^6$ ...................................................... B32B 5/18
[52] U.S. Cl. ........................ 428/304.4; 428/403; 428/407; 604/367; 604/368; 604/369; 604/37
[58] Field of Search ................................ 428/304.4, 403, 428/407; 521/138, 149; 604/367, 368, 369, 378

[56] References Cited

U.S. PATENT DOCUMENTS

| | | | |
|---|---|---|---|
| Re. 32,649 | 4/1988 | Brandt et al. | 604/368 |
| 2,926,116 | 2/1960 | Keim | 162/164 |
| 2,926,154 | 2/1960 | Keim | 260/29.2 |
| 3,332,901 | 7/1967 | Keim | 260/29.2 |
| 3,654,060 | 4/1972 | Goldman | 161/112 |
| 3,661,875 | 5/1972 | Sieja | 260/85.5 |
| 3,758,641 | 9/1973 | Zweigle | 260/874 |
| 3,890,974 | 6/1975 | Kozak | 128/287 |
| 4,062,817 | 12/1977 | Westerman | 260/17.45 |
| 4,076,663 | 2/1978 | Masuda et al. | 260/17.4 |
| 4,076,673 | 2/1978 | Burkholder, Jr. | 260/29.2 |
| 4,093,776 | 6/1978 | Aoki et al. | 428/402 |
| 4,132,695 | 1/1979 | Burkholder | 260/29.6 |
| 4,154,898 | 5/1979 | Burkholder, Jr. | 428/500 |
| 4,190,563 | 2/1980 | Bosley et al. | 260/17.4 |

(List continued on next page.)

FOREIGN PATENT DOCUMENTS

| | | | |
|---|---|---|---|
| 159371 | 10/1985 | European Pat. Off. | A61L 15/00 |
| 0 317 106 | 5/1989 | European Pat. Off. | |
| 0 450 922 | 10/1991 | European Pat. Off. | C08F 8/14 |
| 0 450 923 A2 | 10/1991 | European Pat. Off. | C08F 8/14 |
| 0 450 924 | 10/1991 | European Pat. Off. | C08F 8/14 |
| 0 493 011 A2 | 7/1992 | European Pat. Off. | |
| 0 509 708 A1 | 10/1992 | European Pat. Off. | |
| 0 555 692 A1 | 8/1993 | European Pat. Off. | |
| 56-97450 | 8/1981 | Japan | A61F 13/18 |
| 59-211457 | 11/1984 | Japan | A61L 15/00 |
| 62-112655 | 5/1987 | Japan | C08L 101/00 |
| 63-19215 | 4/1988 | Japan . | |
| 304127 | 12/1989 | Japan | C08J 3/00 |
| 304128 | 12/1989 | Japan | B29B 13/06 |
| 30336 | 7/1990 | Japan | C08J 3/12 |
| 233139 | 9/1990 | Japan | A61F 13/46 |
| 161431 | 6/1992 | Japan | B01D 15/00 |
| 6-370 | 1/1994 | Japan . | |
| WO 90/08789 | 8/1990 | WIPO | C08F 265/02 |
| WO 91/15177 | 10/1991 | WIPO | A61F 13/15 |
| WO 91/15362 | 10/1991 | WIPO | B32B 3/10 |
| WO 91/15368 | 10/1991 | WIPO | B32B 31/30 |
| WO 92/16565 | 10/1992 | WIPO | C08F 2/18 |
| WO 95/19191 | 7/1995 | WIPO . | |

*Primary Examiner*—Elizabeth M. Cole
*Attorney, Agent, or Firm*—Carl J. Roof; Edward J. Milbrada; Mary Catherine Hentz

[57] ABSTRACT

A porous absorbent material that comprises a water-insoluble, water-swellable absorbent polymer. The absorbent material comprises a polyether and/or a polycation bonded to the absorbent polymer whereby the contact angle of blood on a surface of the absorbent material attains from about 0 degree to about 40 degree. Because of the improved wettability with liquids as well as the porous structure, the absorbent material can provide higher absorbent characteristics with liquids, in particular with blood.

29 Claims, 4 Drawing Sheets

U.S. PATENT DOCUMENTS

| | | | |
|---|---|---|---|
| 4,269,188 | 5/1981 | Nishizawa et al. | 128/287 |
| 4,310,593 | 1/1982 | Gross | 428/290 |
| 4,340,706 | 7/1982 | Obayashi et al. | 526/207 |
| 4,413,995 | 11/1983 | Korpman | 604/368 |
| 4,446,261 | 5/1984 | Yamasaki et al. | 524/40 |
| 4,474,949 | 10/1984 | Chatterjee et al. | 536/56 |
| 4,506,052 | 3/1985 | Furukawa et al. | 524/357 |
| 4,541,871 | 9/1985 | Obayashi et al. | 106/197.2 |
| 4,587,308 | 5/1986 | Makita et al. | 525/373 |
| 4,605,401 | 8/1986 | Chmelir et al. | 604/368 |
| 4,624,868 | 11/1986 | Muller | 427/384 |
| 4,625,001 | 11/1986 | Tsubakimoto et al. | 526/88 |
| 4,647,617 | 3/1987 | Saotome | 524/733 |
| 4,654,039 | 3/1987 | Brandt et al. | 604/368 |
| 4,666,983 | 5/1987 | Tsubakimoto et al. | 525/119 |
| 4,676,784 | 6/1987 | Erdman et al. | 604/368 |
| 4,677,174 | 6/1987 | Alexander et al. | 526/240 |
| 4,690,971 | 9/1987 | Flesher et al. | 524/555 |
| 4,693,713 | 9/1987 | Chmelir et al. | 604/368 |
| 4,698,404 | 10/1987 | Cramm et al. | 526/204 |
| 4,715,918 | 12/1987 | Lang | 156/273.1 |
| 4,734,478 | 3/1988 | Tsubakimoto et al. | 527/300 |
| 4,735,987 | 4/1988 | Morita et al. | 524/436 |
| 4,755,562 | 7/1988 | Alexander et al. | 525/113 |
| 4,758,617 | 7/1988 | Tanioku et al. | 524/413 |
| 4,766,173 | 8/1988 | Bailey et al. | 524/819 |
| 4,777,200 | 10/1988 | Dymond et al. | 524/458 |
| 4,783,510 | 11/1988 | Saotome | 525/329.7 |
| 4,820,773 | 4/1989 | Alexander et al. | 525/274 |
| 4,824,901 | 4/1989 | Alexander et al. | 524/555 |
| 4,833,179 | 5/1989 | Young et al. | 522/183 |
| 4,861,539 | 8/1989 | Allen et al. | 264/204 |
| 4,880,858 | 11/1989 | Farrar et al. | 524/60 |
| 4,921,904 | 5/1990 | Sparapany et al. | 525/329.9 |
| 4,950,692 | 8/1990 | Lewis et al. | 521/45 |
| 4,954,562 | 9/1990 | Anderson | 524/779 |
| 4,962,172 | 10/1990 | Allen et al. | 526/318.42 |
| 4,970,267 | 11/1990 | Bailey et al. | 525/344 |
| 4,973,632 | 11/1990 | Nagasuna et al. | 526/200 |
| 4,980,434 | 12/1990 | Farrar et al. | 526/240 |
| 4,997,714 | 3/1991 | Farrer et al. | 428/394 |
| 5,102,597 | 4/1992 | Roe et al. | 264/126 |
| 5,118,719 | 6/1992 | Lind | 521/92 |
| 5,122,544 | 6/1992 | Bailey et al. | 521/40.5 |
| 5,124,188 | 6/1992 | Roe et al. | 428/72 |
| 5,147,956 | 9/1992 | Allen | 526/318.42 |
| 5,149,334 | 9/1992 | Lahrman et al. | 604/367 |
| 5,149,335 | 9/1992 | Kellenberger et al. | 604/372 |
| 5,154,713 | 10/1992 | Lind | 604/358 |
| 5,171,781 | 12/1992 | Farrar et al. | 524/547 |
| 5,180,622 | 1/1993 | Berg et al. | 428/192 |
| 5,195,999 | 3/1993 | Harada et al. | 604/368 |
| 5,206,205 | 4/1993 | Tsai | 502/402 |
| 5,236,965 | 8/1993 | Engelhardt et al. | 521/142 |
| 5,250,642 | 10/1993 | Ahmed et al. | 526/240 |
| 5,264,471 | 11/1993 | Chmelir | 524/35 |
| 5,280,079 | 1/1994 | Allen et al. | 525/329.2 |
| 5,286,827 | 2/1994 | Ahmed | 526/287 |
| 5,338,766 | 8/1994 | Phan et al. | 521/63 |

5,985,432

POROUS ABSORBENT MATERIALS HAVING MODIFIED SURFACE CHARACTERISTICS AND METHODS FOR MAKING THE SAME

CROSS-REFERENCE TO RELATED APPLICATION

This is a continuation of application Ser. No. 08/224,454, filed Apr. 7, 1994, now abandoned, which is a continuation-in-part of application Ser. No. 08/197,916, filed Feb. 17, 1994, now abandoned.

FIELD OF THE INVENTION

The present invention relates to absorbent materials which, upon contacting liquids such as water or body exudates, swell and imbibe such liquids. More specifically, the present invention relates to porous absorbent materials having modified surface characteristics. Such porous absorbent materials have improved absorption characteristics with liquids. The present invention has particular applicability to absorbent articles such as diapers, adult incontinence pads, sanitary napkins, and the like. The invention also relates to processes for producing such materials and to absorbent articles containing such materials.

BACKGROUND OF THE INVENTION

Water-insoluble, water-swellable, hydrogel-forming absorbent polymers are capable of absorbing large quantities of liquids such as water, blood, body exudates (e.g., urine, menstrual fluid), industrial fluids and household fluids and are further capable of retaining such absorbed liquids under moderate pressures. The absorption characteristics of such polymer materials make them especially usefull for incorporation into absorbent articles such as diapers, sanitary napkins, tampons, and the like.

In general, conventional absorbent polymer materials have good or required absorption characteristics to water and urine; however, there still remains poor distribution and dispersion with certain liquids. In particular, they have poor absorption characteristics for certain liquids, specifically for blood or menstrual fluid. More specifically, upon contacting blood or menstrual fluid, absorbent polymer materials do not show enough absorption characteristics, especially the rate of blood absorption due to their poor distribution and dispersion of blood.

Such poor distribution and dispersion of blood is mainly caused by poor wettability with blood. In general, ability of the distribution and dispersion of blood can be evaluated by measuring the contact angle of blood on the surface of absorbent polymer material. Since contact angles of conventional absorbent polymer materials are in the range of from about 30 degree to about 90 degree or more, desired wettability with blood cannot be obtained whereby the poor distribution and dispersion of blood are caused in the absorbent polymer materials.

One attempt to improve such absorption characteristics is disclosed in U.S. Pat. No. 4,190,563 (Rosley et al.), issued Feb. 20, 1980, wherein the wettability with blood is improved by surface treatment of particulate absorbent polymer materials using polyethers. The disclosed absorbent polymer materials can be effectively wetted with blood; however, the distribution and dispersion of the blood into and among the absorbent polymer materials is not fully improved because of their high resistance to liquid flow within the polymer materials due to lack of capillary or liquid transport channels, and insufficient specific surface area of the polymer materials. Therefore, the absorption characteristics with blood is not satisfactory and there remains a need to improve further the distribution and dispersion of blood through and among absorbent polymer materials.

In addition, since the polyether are just coated or physically bonded on the surface of absorbent polymer materials, such polyether can be washed away from the absorbent polymer materials by succeeding application of liquids.

Consequently, there remains a need for further improvements in such absorbent materials.

Therefore, one object of the present invention is to provide a porous absorbent material which has improved absorption characteristics with liquids.

Another object of the present invention is to improve distribution and dispersion of liquids in an absorbent material.

Yet another object of the present invention is to improve the rate of absorption of an absorbent material, especially for blood.

Still another object of the present invention is to provide an absorbent material which is not affected by succeeding application of liquids.

Yet another object of the present invention is to provide a method for making such absorbent materials.

Still another object of the present invention is to provide absorbent disposable articles, such as diapers, sanitary napkins, tampons, and the like, which have improved absorption characteristics with body exudates.

SUMMARY OF THE INVENTION

Briefly stated, the present invention relates to porous absorbent materials having modified surface characteristics. In an aspect, a porous absorbent material comprises a water-insoluble, water-swellable polymer, wherein the contact angle of blood on a surface of the absorbent material is from about 0 degree to about 40 degree.

In another aspect of the invention, a porous absorbent material comprises a water-insoluble, water-swellable polymer, a positive-charge supplying compound bonded to the water-insoluble, water-swellable polymer; and a non-ionic hydrophilic compound bonded to the water-insoluble, water-swellable polymer.

The present invention further relates to an absorbent article. The absorbent article comprises (a) a liquid pervious topsheet; (b) a liquid impervious backsheet; and (c) an absorbent core positioned between the topsheet and the backsheet. The absorbent core comprises at least one porous absorbent material of the present invention.

The present invention further relates to methods for making porous absorbent materials having modified surface characteristics. In further aspect of the invention, a porous absorbent material is produced by (a) applying a first surface modification compound onto a portion of a surface of a water-insoluble, water swellable absorbent polymer, wherein the first surface modification compound has a function for modifying surface characteristics of the absorbent polymer; (b) swelling the absorbent polymer by absorbing water; and (c) removing a portion of the water while maintaining the water-insoluble, water-swellable polymer in substantially the swollen state, thereby forming a porous structure in the absorbent material.

In still another aspect of the invention, a porous absorbent material is produced by (aa) maling a swollen water-insoluble, water-swellable polymer from polymerizable, unsaturated, acid-containing monomers using an aqueous solution polymerization method; (bb) applying a first surface modification compound onto a portion of a surface of the swollen water-insoluble, water-swellable polymer, wherein the first surface modification compound having a function for modifyng surface characteristics of the swollen water-insoluble, water-swellable polymer; and (c) removing a portion of the water while maintaining the water-insoluble, water-swellable polymer in substantially the swollen state, thereby forming a porous structure in the absorbent material.

In yet another aspect of the invention, a porous absorbent material is produced by (A) making a porous water-insoluble, water-swellable polymer; and (B) applying a first surface modification compound onto a surface of the porous water-insoluble, water-swellable polymer, wherein the first surface modification compound has a function for modifying surface characteristics of the porous water-insoluble, water-swellable polymer.

DETAILED DESCRIPTION OF POROUS ABSORBENT MATERIALS OF THE INVENTION

Porous absorbent materials of the present invention are capable of absorbing large quantities of liquids such as water, blood, body exudates (e. g., urine or menstrual fluid), industrial fluids and household fluids and are capable of retaining such liquids under moderate pressure. Typically, the porous absorbent materials of the present invention will swell generally isotropically and absorb rapidly the liquids.

Porous absorbent materials of the present invention comprise a water-insoluble, water-swellable polymer capable of absorbing large quantities of liquids. (Such absorbent polymer is commonly referred to as a hydrogel, hydrocolloid, superabsorbent polymer.) The porous absorbent materials preferably comprise substantially water-insoluble, water-swellable absorbent polymers. The specific absorbent polymers for use in the present invention will be described in detail hereinafter.

In one aspect of the present invention, a porous absorbent material having modified surface characteristics comprises a water-insoluble, water-swellable absorbent polymer. The porous absorbent material has the contact angle of blood on a surface of the porous absorbent material from about 0 degree to about 40 degree.

It should be noted that in this aspect of the invention the porous absorbent material can be used to absorb a variety of liquids, non-limiting examples of which include water, blood, body exudates, industrial fluids and household fluids. To describe the characteristic of the improved porous absorbent material, blood has been selected as a representative liquid material; an porous absorbent material in accordance with this aspect of the invention will exhibit the specified characteristics with blood as the absorbed fluid medium.

The term "blood" used herein should be understood in general. A typical example of content of "normal blood" is disclosed in a paper written by H. Nagorski et al. and entitled "SUPERABSORBENT POLYMERS IN FEMININE HYGIENE APPLICATIONS" in the American publication named "THE NEW NOWOVENS WORLD" (pp. 101–106; Fall, 1992), which is incorporated herein by reference.

Figure 1:
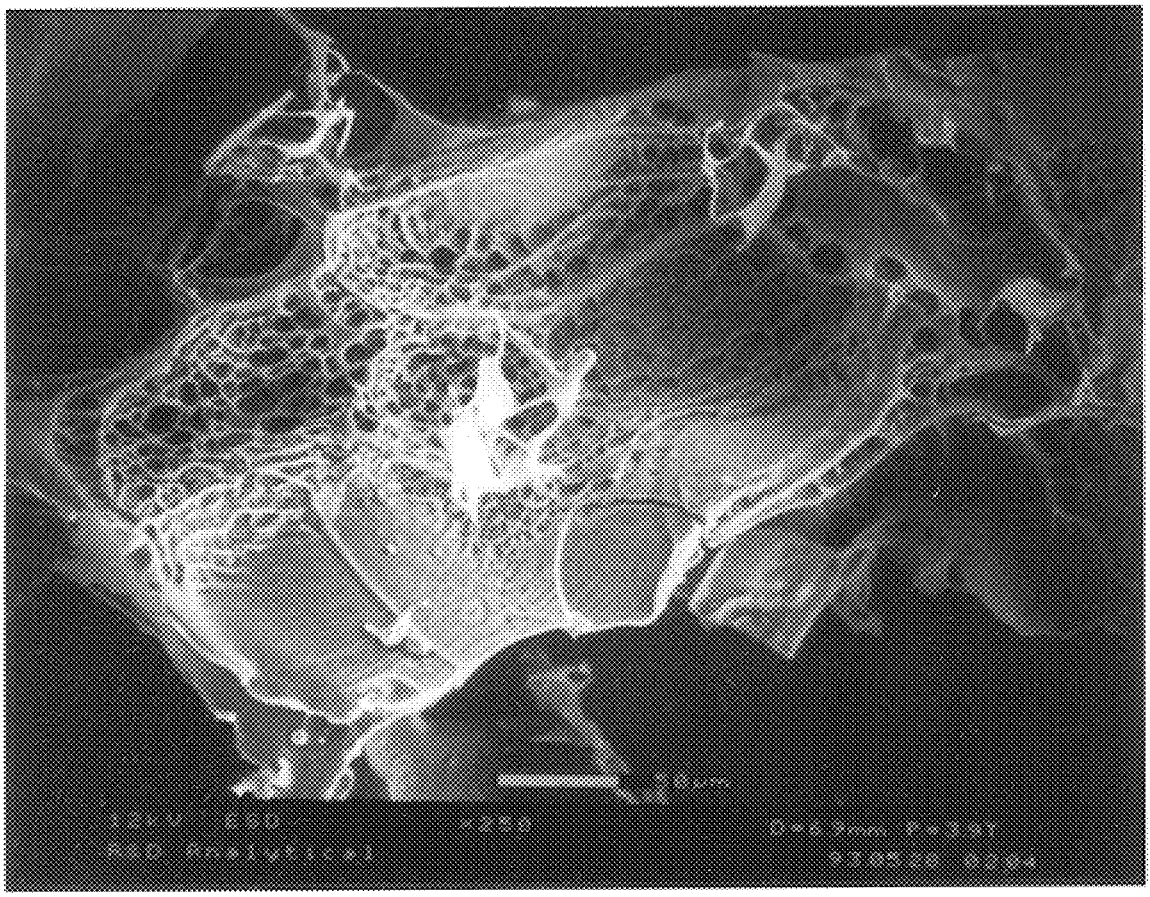
FIG. 1 is a scanning electronic micrograph (magnification 250×) of a section of a porous absorbent material of one embodiment of the present invention.
Figure 2:
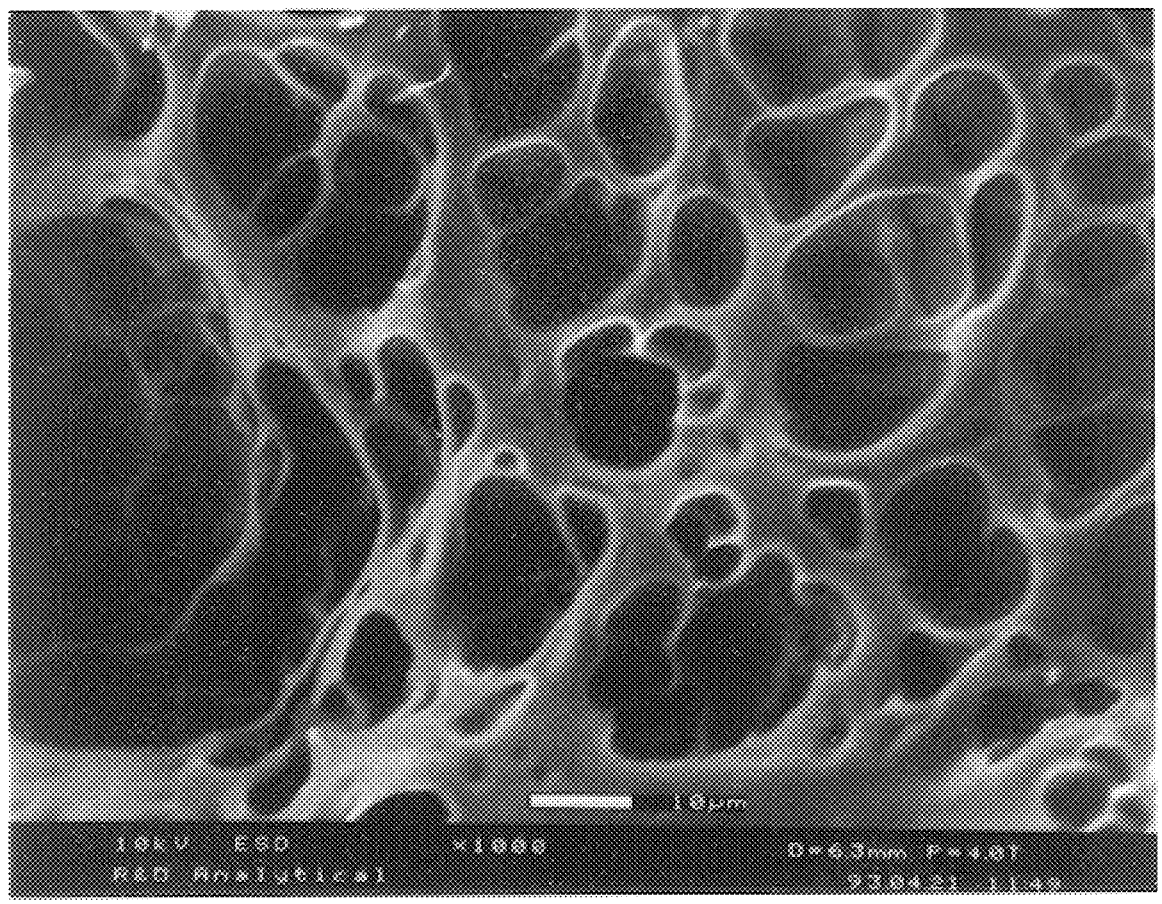
FIG. 2 is an enlarged portion (magnification 1000×) of the porous absorbent material shown in FIG. 1.
Figure 3:
FIG. 3 is a scanning electronic micrograph (magnification 250×) of a section of a porous absorbent material of another embodiment of the present invention.
Figure 4:
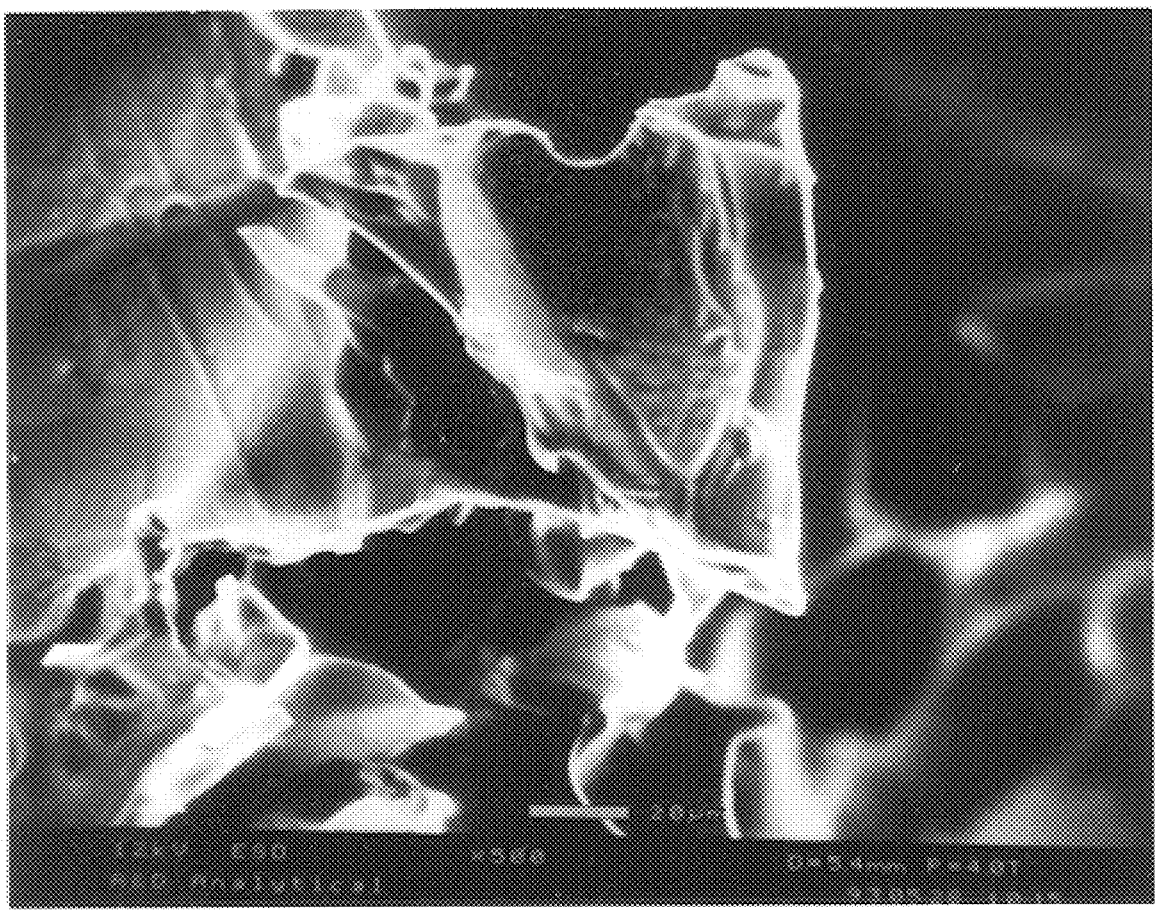
FIG. 4 is an enlarged portion (magnification 500×) of the porous absorbent material shown in FIG. 3.

As used herein, the term "porous" means a structure forming walls surrounding and defining cellular voids of absorbent polymers when substantially dry. In general a porous structure of absorbent material can provide the porous absorbent material with low density and/or high specific surface area. Under microscopic observations, walls formed in a porous absorbent material, for example, show the sponge-like appearance as shown in FIGS. 1 and 2, and walls of another porous absorbent material show the withered leaf-like appearance as can be especially seen in FIGS. 3 and 4.

In preferred embodiments, the porous absorbent materials have a bulk density of from about 0.01 g/cc to about 0.4 g/cc, preferably from about 0.03 g/cc to about 0.35 g/cc, and more preferably from about 0.06 g/cc to about 0.3 g/cc.

In alternative preferred embodiments, the porous absorbent materials have a specific surface area of at least about 400 $cm^2/g$, preferably at least about 600 $cm^2/g$, and more preferably at least about 1,000 $cm^2/g$. A method of determining the specific surface area of a sample of the porous absorbent materials is also described in the TEST METHODS section.

In general, the wettability with the liquids can be defined in terms of contact angles and the surface tension of the liquids and solids involved. This is discussed in detail in the American Chemical Society Publication entitled "Contact Angle, Wettability, and Adhesion" edited by Robert F. Gould and copyrighted in 1964, which is incorporated by reference.

Due to the porous structure of the absorbent material and the improved wettability with liquids (i.e. the low contact angle on the surface) of the porous absorbent material, the liquid distribution and dispersion of blood and other liquids such as urine and water around and through the porous absorbent material can be improved. Thus, the porous absorbent material can swell isotropically and absorb rapidly the liquids. A method of determining the contact angle of a sample is described in the TEST METHODS section.

In preferred embodiments, the porous absorbent material of the present invention further comprises a hydrophilic compound having a function for modifying surface characteristics of the porous absorbent materials. A variety of hydrophilic compounds that have such surface modifying functions will be described hereinafter in detail. The term "surface characteristic" herein used means that a physical characteristic at a surface of a material when contacting with liquids. For example, the wettability of liquids and the contact angle of liquids on a surface of absorbent material are included in such surface characteristics. The term "modify" herein used means that to change the characteristics, or to increase or decrease the degree of the characteristics.

Both types of reactive and non-reactive hydrophilic compounds can be used as the hydrophilic compound. As used herein, the term "reactive" means a hydrophilic compound which can react with the absorbent polymer under the process condition of the present invention. In other words, such hydrophilic compound comprises at least one reactive functional group that can, under the process condition, form a covalent bond with the absorbent polymer, or effective number of cationic groups for the ionic bond to the absorbent polymer through the electrostatic interaction. Therefore, the reactive hydrophilic compound forms a chemical bond between the hydrophilic compound and the absorbent polymer. Any type of chemical bonds including covalent bonds and ionic bonds can be formed between the reactive hydrophilic compound and the absorbent polymer. Such chemical bonds must be strong enough to prevent the reactive hydrophilic compound on the surface of the porous absorbent material from being washed away by succeeding application of liquids (e.g., water, urine, menstrual fluid, etc.). In a preferred embodiment, a covalent bond or an ionic bond can be formed as one of such chemical bonds. For example, the covalent bond generally arises as a result of the formation of ester, amide (imide), or urethane bonds by reaction of the functional group of the hydrophilic compound with a carboxyl group of the absorbent polymer.

On the other hand, the term "non-reactive" means a hydrophilic compound which does not react with the absorbent polymer under the process condition of the present invention. In other words, such hydrophilic compound does not comprise any reactive functional group that can form a covalent bond with the absorbent polymer under the process condition nor effective number of cationic groups for the ionic bond to the absorbent polymer. Therefore, the non-reactive hydrophilic compounds which are merely capable of physically associating to, physically connecting to or physically bonding to the absorbent polymer through intermolecular interactions.

In some of the preferred embodiments, a spacer can be present between the hydrophilic compound and the absorbent polymer, to form a chemical bond between the hydrophilic compound and the absorbent polymer. The spacer in use herein should have at least one atom, capable of making such chemical bond or connection between the hydrophilic compound and the absorbent polymer.

In more preferred embodiments of the present invention, the hydrophilic compound can be either a positive-charge supplying compound or a non-ionic hydrophilic compound. The non-ionic hydrophilic compound can be either a reactive polyether having at least one reactive functional group or a non-reactive polyether which is capable of physically associating to, physically connecting to or physically bonding to the absorbent polymer through intermolecular interactions.

Preferred non-reactive polyethers are described in greater detail, for example, in U.S. Pat. No. 4,190,563 (Bosley et al.), issued Feb. 26, 1980, which is incorporated by reference. Some of non-reactive polyethers preferably used are described hereinafter. The backbone of the non-reactive polyethers can be expressed by the following formula:

$$R(C_2H_4O)_a(C_3H_6O)_b(C_2H_4O)_cR$$

where a+c represents the total number of oxyethylene units and b the number of oxypropylene units and where a+c or b can be zero, and R is a non-reactive functional group unable to bond chemically to the absorbent polymer under the process condition of the present invention and is preferably independently selected from H—, HO—, $CH_3O$—, $CH_3CH_2O$—, and so on.

The molecular weight of a non-reactive polyether can typically be from 200 to 20,000.

The non-reactive polyether can be a polyoxyethylene polymer, i.e. a polyethylene glycol, in which case b in the above formula is zero. Polyethylene glycols are water-soluble. Preferred polyethylene glycols are those having a molecular weight of from 200 to 3,000.

The non-reactive polyether can be a polyoxypropylene polymer, i.e. a polypropylene glycol, in which case a+c in the above formula is zero. Polypropylene glycol are not soluble in water. Preferred polypropylene glycols are those having a molecular weight of from 400 to 4,000.

The non-reactive polyether can also be a water-soluble or a water-insoluble polyoxyethylene-polyoxypropylene block copolymer. By a water-soluble non-reactive polyether is meant one which is soluble to the extent of more than 1% in water at 25° C., i.e. a solubility of greater than 1 gram in 100 grams of water. In water-soluble polyoxyethylene-polyoxypropylene copolymers the weight of the oxyethylene units exceeds about 15% by weight of the total compound. Preferred polyoxyethylene-polyoxypropylene copolymers are those which are liquid at room temperature. Preferred water-soluble copolymers are those having a molecular weight of from 1,000 to 4,000.

In more preferred embodiments, the non-reactive polyether is selected from the group consisting of a non-reactive polyethylene glycol (PEG), a non-reactive polypropylene glycol, and a non-reactive poly(oxyethylene-oxypropylene) copolymer.

Preferred reactive polyethers have at least one reactive functional group capable of forming a chemical bond onto the surface of the absorbent polymer through a covalent bond or an ionic bond.

In preferred embodiments, the reactive polyether capable of forming a covalent bond to the absorbent polymer will have at least one reactive functional group as the terminal group, which has the repeat units of oxyethylene or oxypropylene, and/or a mixture thereof. The functional group of the reactive polyether can be any chemical group reactive with the absorbent polymer, such as a halogen group, a carboxyl group, an amino group, or an epoxy group.

The preferred reactive polyethers are described in greater detail hereinafter. The backbone of the reactive polyether can be expressed by the following formula:

$$X(C_2H_4O)_a(C_3H_6O)_b(C_2H_4O)_cY$$

where at least one of X and Y is a reactive functional group capable of bonding to the absorbent polymer, i.e. a halogen group, a carboxyl group, an epoxy group and so on, and where a+c represents the total number of oxyethylene units and b the number of oxypropylene units, and where a+c or b can be zero. X and Y can be either the same functional group or different functional groups.

The molecular weight of the reactive polyethers can typically be from 200 to 20,000.

The reactive polyether can be a polyoxyethylene polymer having at least one reactive functional group, i.e. a polyethylene glycol terminating with a functional group, in which case b in the above formula is zero. Reactive polyethylene glycol derivatives are water-soluble. Preferred reactive polyethylene glycol derivatives are those having a molecular weight of from 200 to 3,000.

The reactive polyether can be a polyoxypropylene polymer having at least one reactive functional group, i.e. a reactive polypropylene glycol terminating with a functional group, in which case a+c in the above formula is zero. Reactive polypropylene glycol derivatives are generally not soluble in water. Preferred reactive polypropylene glycol derivatives are those having a molecular weight of from 400 to 4,000.

The reactive polyether can also be a water-soluble or a water-insoluble polyoxyethylene-polyoxypropylene block copolymer. By a water-soluble reactive polyether is meant one which is soluble to the extent of more than 1% in water at 25° C., i.e. a solubility of greater than 1 gram in 100 grams of water. In water-soluble polyoxyethylene-polyoxypropylene copolymers the weight of the oxyethylene units exceeds about 15% by weight of the total compound. Preferred polyoxyethylene-polyoxypropylene copolymers are those which are liquid at room temperature. Preferred water-soluble copolymers are those having a molecular weight of from 1,000 to 4,000.

In more preferred embodiments, the reactive polyether is selected from the group consisting of a reactive polyethylene glycol (PEG), a reactive polypropylene glycol, and a reactive poly(oxyethylene-oxypropylene) copolymer.

In alternative and preferred embodiments, a positive-charge supplying compound can be used as the reactive hydrophilic compound chemically bonded to the absorbent polymer. The positive-charge supplying compound can supply the absorbent polymer with a positive-charge thereby forming an ionic bond between the absorbent polymer and the positive-charge supplying compound.

In further alternative and more preferred embodiments, a polycation can be used as the positive-charge supplying compound chemically bonded to the absorbent polymer. The polycation is a polymer having more than one positively-charged groups capable of forming ionic bonds to the absorbent polymer. In preferred embodiments, the polycation preferably used is selected from the group consisting of (1) polymers having primary amine groups (e.g. polyvinylamine, polyallyl amine); (2) polymers having secondary amine groups (e.g. polyethyleneimine); (3) polymers having tertiary amine groups (e.g. poly N, N-dimethylalkyl amine); and (4) polymers having quaternary amine groups (e.g. polydiallyl dimethyl ammonium chloride).

More preferred polycation for use is a polyamine having primary or secondary amine groups such as a polyallylamine, polyvinyl amine, or a polyimine such as a polyethyleneimine.

In further more preferred embodiments, a polycation having oxyethylene repeat units or oxypropylene repeat units can be used as the positive-charge supplying compound. For example, an ethoxylated or a propoxylated product of an amino compound that has oxyethylene units, oxypropylene units or both units thereof can also be used as the polycation to form ionic bonds to the absorbent polymer. The oxyethylene or oxypropylene units of such polycation can have the same formula as described above. Amino compounds useful in the present invention will be described in detail hereinafter.

Most preferred polycation for use is a cationic amino-epichlorohydrin adduct which is the reaction product between epichlorohydrin and a amino compound such as a monomeric or polymeric amine so that the resulting reaction product has at least two cationic functional groups. These adducts can be in the form of monomeric compounds (e.g., the reaction product of epichlorohydrin and ethylene diamine), or can be in polymeric form (e.g., the reaction product between epichlorohydrin, and polyamide-polyamines or polyethyleneimines). The polymeric versions of these cationic amino-epichlorohydrin adducts are typically referred to as "resins."

One type of amino compounds which can be used for maling the ethoxylated or propoxylated product, and can be reacted with epichlorohydrin to form adducts useful in the present invention comprises monomeric di-, tri- and higher amines having primary or secondary amino groups in their structures. Examples of useful diamines of this type include bis-2-aminoethyl ether, N,N-dimethylethylenediamine, piperazine, and ethylenediamine. Examples of useful tri-amines of this type include N-aminoethyl piperazine, and dialkylene triamines such as diethylenetriamine, and dipropylenetriamine.

Such amine materials are reacted with epichlorohydrin to form the cationic amino-epichlorohydrin adducts useful as reactive hydrophilic compound herein. Preparation of these adducts, as well as a more complete description of the adducts themselves, can be found in U.S. Pat. No. 4,310,593 (Gross), issued Jan. 12, 1982, and in Ross et al, J. Organic Chemistry, Vol. 29, pp. 824–826 (1964). Both of these documents are incorporated by reference.

In addition to monomeric amines, polymeric amines such as polyethyleneimines can also be used as the amino compound. A particularly desirable amino compound which can be reacted with epichlorohydrin to form preferred cationic polymeric adduct resins useful herein comprise certain polyamide-polyamines derived from polyalkylene polyamines and saturated C3–C10 di-carboxylic acids. Epichlorohydrin/polyamide-polyamine adducts of this kind are water-soluble, thermosetting cationic polymers which are well known in the art as wet strength resins for paper products.

In the preparation of polyamide-polyamines used to form this preferred class of cationic polymeric resins, a dicarboxylic acid is first reacted with a polyalkylene-polyamine, preferably in aqueous solution, under conditions such as to produce a water-soluble, long chain polyamide containing the recurring groups —NH($C_nH_{2n}$HN)$_x$—CORCO— where n and x are each 2 or more and R is the C1 to C8 alkylene group of the dicarboxylic acid.

A variety of polyalkylene polyamines including polyethylene polyamines (e.g. polyethyleneimine or polyvinylamine), polypropylene polyamines (e.g. polyallylamine), polybutylene polyamines and so on can be employed to prepare the polyamide-polyamine, of which the polyethylene polyamines represent an economically preferred class. More specifically, preferred polyalkylene polyamines used to prepare the cationic polymeric resins herein are polyamines containing two primary amine groups and at least one secondary amine group in which the nitrogen atoms are linked together by groups of the formula —$C_nH_{2n}$— where n is a small integer greater than unity and the number of such groups in the molecule ranges from two up to about eight and preferably up to about four. The nitrogen atoms can be attached to adjacent carbon atoms in the group —$C_nH_{2n}$— or to carbon atoms further apart, but not to the same carbon atom. Also contemplated is the use of such polyamines as diethylenetriamine, triethylene tetramine, tetraethylenepentamine, dipropylenetriamine, and the like, which can be obtained in reasonably pure form. Of all the foregoing, the most preferred are the polyethylene polyamines containing from two to four ethylene groups, two primary amine groups, and from one to three secondary amine groups.

In preferred embodiments, the polycation is selected from the group consisting of (1) ethoxylated monomeric amine; (2) ethoxylated polyamine; and (3) ethoxylated polyimine. For example, the ethoxylated monomeric amine is tetraethylene pentamine ethoxylated with 15 moles (average) of ethylene oxide at each hydrogen site on each nitrogen (TEPA-$E_{15}$); the ethoxylated polyamine is polyallylamine ethoxylated with 15 moles (average) of ethylene oxide at hydrogen sites on nitrogen atoms; the ethoxylated polyimine is polyethyleneimine ethoxylated with 15 moles (average) of ethylene oxide at hydrogen sites on nitrogen atoms.

Also contemplated for use herein are polyamine precursor materials containing at least three amino groups with at least one of these groups being a tertiary amino group. Suitable polyamines of this type include methyl bis(3-aminopropyl) amine, methyl bis(2-aminoethyl)amine, N-(2-aminoethyl) piperazine, 4,7-dimethyltriethylenetetramine and the like.

The dicarboxylic acids which can be reacted with the foregoing polyamines to form the polyamide-polyamine precursors of the preferred cationic polymeric resins useful herein comprise the saturated aliphatic C3–C10 dicarboxylic acids. More preferred are those containing from 3 to 8 carbon atoms, such as malonic, succinic, glutaric, adipic, and so on, together with diglycolic acid. Of these, diglycolic acid and the saturated aliphatic dicarboxylic acids having from 4 to 6 carbon atoms in the molecule, namely, succinic, glutaric and adipic are most preferred. Blends of two or more of these dicarboxylic acids can also be used, as well as blends of one or more of these with higher saturated aliphatic dicarboxylic acids such as azelaic and sebacic, as long as the resulting long chain polyamide-polyamine is water-soluble or at least water-dispersible.

The polyamide-polyamine materials prepared from the foregoing polyamines and dicarboxylic acids are reacted with epichlorohydrin to form the cationic polymeric aminoepichlorohydrin resins preferred for use herein as the reactive hydrophilic compound. Preparation of such materials is describe in greater detail in U.S. Pat. No. 2,926,116 (Keim), issued Feb. 23, 1960, U.S. Pat. No. 2,926,154 (Keim), issued Feb. 23, 1960, and U.S. Pat. No. 3,332,901 (Keim), issued Jul. 25, 1967, all of which are incorporated by reference.

A porous absorbent material of another aspect of the present invention comprises, a positive-charge supplying compound bonded to the absorbent polymer, and a non-ionic hydrophilic compound bonded to the absorbent polymer.

In a preferred embodiment, the contact angle of blood on a surface of the porous absorbent material is from about 0 degree to about 40 degree.

Any of the above described positive-charge supplying compounds can be used. Preferred are the above described polycations which can bond to the absorbent polymer through the ionic bond. In this aspect of the invention, the non-ionic hydrophilic compound can include the above described reactive polyethers which are capable of chemically bonding to the absorbent polymer, as well as the non-reactive polyethers which are merely capable of physically associating to, physically connecting to or physically bonding to the absorbent polymer through intermolecular interactions.

It is noted that all of the above described porous absorbent materials of the present invention can have a number of shapes and sizes. For example, the porous absorbent materials are typically in the form of particles, sheets, films, cylinders, blocks, fibers, filaments, or other shaped elements. The term "particle" as used herein describes the porous absorbent materials of the present invention can be formed into granules, pulverulents, spheres, flakes, fibers, aggregates or agglomerates, and the size of the porous absorbent materials will generally range in size from between about 1 micron to about 2000 microns, more preferably between about 20 microns to about 1000 microns. The term "sheet" as used herein describes the porous absorbent materials of the present invention can be formed within a thickness at least about 0.2 mm. The sheets will preferably have a thickness between about 0.5 mm and about 10 mm, typically from about 1 mm to about 3 mm.

WATER-INSOLUBLE WATER-SWELLABLE POLYMER MATERIALS

The absorbent polymers for use in the present invention are hydrogel-forming. Preferably, the absorbent polymers suitable for use can be a crosslinked polyelectrolyte. More preferably, the crosslinked polyelectrolyte can have a multiplicity of anionic functional groups, such as sulfonic acid, and more typically carboxyl groups. In preferred embodiments, the crosslinked polyelectrolyte is selected from the group consisting of a crosslinked polyacrylate sodium, a crosslinked polymethacrylate sodium, a crosslinked polyacrylate potassium, a crosslinked polymethacrylate potassium, a crosslinked starch grafted polyacrylate, a crosslinked starch grafted polymethacrylate, a crosslinked polyvinyl alcohol grafted polyacrylate, a crosslinked polyvinyl alcohol grafted polymethacrylate, a crosslinked carboxy methyl cellulose, a crosslinked cellulose grafted polyacrylate, and a crosslinked cellulose grafted methacrylate.

Some of preferred crosslinked polyelectrolytes are made from polymerizable, unsaturated, acid-containing monomers. Thus, such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids, and mixtures thereof.

Some non-acid monomers can also be included, usually in minor amounts, in preparing the crosslinked polyelectrolyte herein. Such non-acid monomers can include, for example, the water-soluble or water-dispersible esters of the acid-containing monomers, as well as monomers which contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups and quaternary ammonium salt groups. These non-acid monomers are well-known materials and are described in greater detail, for example, in U.S. Pat. No. 4,076,663 (Masuda et al), issued Feb. 28, 1978, and in U.S. Pat. No. 4,062,817 (Westerman), issued Dec. 13, 1977, both of which are incorporated by reference.

Olefinically unsaturated carboxylic acid and carboxylic acid anhydride monomers include the acrylic acids typified by acrylic acid itsel, methacrylic acid, ethacrylic acid, a-chloroacrylic acid, a-cyanoacrylic acid, b-methylacrylic acid a (crotonic acid), a-phenylacryllic acid, b-acryloxypropionic acid, sorbic acid, a-chlorosorbic acid, angelic acid, cinnamic acid, p-chloro cinnamic acid, b-sterylacrylic acid, itaconic acid, citroconic acid, mesaconic acid, glutaconic acid, aconitic acid, maleic acid, fumaric acid, tricarboxyethylene and maleic acid anhydride. Olefinically unsaturated sulfonic acid monomers include aliphatic or aromatic vinyl sulfonic acids such as vinylsulfonic acid, allyl sulfonic acid, vinyltoluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxy propyl sulfonic acid and 2-acrylamide-2-methylpropane sulfonic acid.

Preferred crosslinked polyelectrolyte for use in the present invention contain carboxy groups. These polymers include hydrolyzed starch-acrylonitrile graft copolymers, partially neutralized starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Most preferred crosslinked polyelectrolyte for use in the invention are slightly network crosslinked polymers of partially neutralized polyacrylic acids and starch derivatives thereof. Most preferably, the crosslinked polyelectrolyte comprise from about 50 to about 95%, preferably about 75%, neutralized, slightly network crosslinked, polyacrylic acid (i.e. poly (sodium acrylate/acrylic acid)).

As described above, the crosslinked polyelectrolyte are polymer materials that are slightly network cross linked. Network crosslinking serves to render the polymer materials water-insoluble and, in part, determines the absorptive capacity and extractable polymer content characteristics of the absorbent material. Processes for network crosslinking the polymers and typical network crosslinking agents are described in greater detail in the hereinbefore-referenced U.S. Pat. No. 4,076,663.

The crosslinked polyelectrolyte particles can be formed in any conventional manner. Typical and preferred processes for producing the crosslinked polyelectrolyte are described in U.S. Pat. No. Re. 32,649 (Brandt et al), issued Apr. 19, 1988, U.S. Pat. No. 4,666,983 (Tsubakimoto et al), issued Can 19, 1987, and U.S. Pat. No. 4,625,001 (Tsubakimoto et al), issued Nov. 25, 1986, all of which are incorporated by reference.

Preferred methods for forming the crosslinked polyelectrolyte are those that involve aqueous solution or other solution polymerization methods. As described in the above-referenced U.S. Pat. No. Re. 32,649, aqueous solution polymerization involves the use of an aqueous reaction mixture to carry out polymerization to form the crosslinked polyelectrolyte. The aqueous reaction mixture is then subjected to polymerization conditions which are sufficient to produce in the mixture, substantially water-insoluble, slightly network crosslinked polymer material.

More specifically, the aqueous solution polymerization method for producing the crosslinked polyelectrolyte comprises the preparation of an aqueous reaction mixture in which to carry out polymerization to form the desired crosslinked polyelectrolyte. One element of such a reaction mixture is the acid group-containing monomer material which will form the "backbone" of the crosslinked polyelectrolyte to be produced. The reaction mixture will generally comprise about 100 parts by weight of the monomer material. Another component of the aqueous reaction mixture comprises a network crosslinking agent. Network crosslinking agents useful in forming the crosslinked polyelectrolyte are described in more detail in the above-referenced U.S. Pat. No. Re. 32,649, U.S. Pat. No. 4,666, 983, and U.S. Pat. No. 4,625,001. The network crosslinking agent will generally be present in the aqueous reaction mixture in an amount of from about 0.001 mole percent to about 5 mole percent based on the total moles of monomer present in the aqueous mixture (about 0.01 to about 20 parts by weight, based on 100 parts by weight of the monomer material) free radical initiator including, for example, peroxygen compounds such as sodium, potassium, and ammonium persulfates, caprylyl peroxide, benzoyl peroxide, hydrogen peroxide, cumene hydroperoxides, tertiary butyl diperphthalate, tertiary butyl perbenzoate, sodium peracetate, sodium percarbonate, and the like. Other optional components of the aqueous reaction mixture comprise the various non-acidic co-monomer materials including esters of the essential unsaturated acidic functional group-containing monomers or other co-monomers containing no carboxylic or sulfonic acid functionalities at all.

The aqueous reaction mixture is subjected to polymerization conditions which are sufficient to produce in the mixture substantially water-insoluble, absorbent, hydrogel-forming, slightly network crosslinked polymer materials. The polymerization conditions are also discussed in more detail in the three abovereferenced patents. Such polymerization conditions generally involve heating (thermal activation techniques) to a polymerization temperature from about 0° C. to about 100° C., more preferably from about 5° C. to about 40° C. Polymerization conditions under which the aqueous reaction mixture is maintained can also include, for example, subjecting the reaction mixture, or portions thereof, to any conventional form of polymerization activating irradiation. Radioactive, electronic, ultraviolet, or electromagnetic radiation are alternative conventional polymerization techniques. The resulting polymerization product is a swollen water-insoluble hydrogel. The swollen water-insoluble hydrogel is used in some preferred processes for making porous absorbent materials as described hereinafter.

The acid functional groups of the polymer materials formed in the aqueous reaction mixture are also preferably neutralized. Neutralization can be carried out in any conventional manner which results in at least about 25 mole percent, and more preferably at least about 50 mole percent, of the total monomer utilized to form the polymer material being acid group-containing monomers that are neutralized with a salt-forming cation. Such salt-forming cations include, for example, alkali metals, ammonium, substituted ammonium and amines as discussed in further detail in the above-references U.S. Pat. No. Re. 32,649.

While it is preferred that the crosslinked polyelectrolyte be manufactured using an aqueous solution polymerization process, it is also possible to carry out the polymerization process using multi-phase polymerization processing techniques such as inverse emulsion polymerization or inverse suspension polymerization procedures. In the inverse emulsion polymerization or inverse suspension polymerization procedures, the aqueous reaction mixture as hereinbefore described is suspended in the form of tiny droplets in a matrix of a water-immiscible, inert organic solvent such as cyclohexane. The resultant crosslinked polyelectrolyte are generally spherical in shape. Inverse suspension polymerization procedures are described in greater detail in U.S. Pat. No. 4,340,706 (Obaysashi et al), issued Jul. 20, 1982, U.S. Pat. No. 4,506,052 (Flesher et al), issued Mar. 19, 1985, and U.S. Pat. No. 4,735,987 (Morita et al), issued Apr. 5, 1988, all of which are incorporated by reference.

Preferred crosslinked polyelectrolyte of the present invention are those which exhibit a high absorptive capacity. Absorptive capacity refers to the capacity of a given polymer material to absorb liquids with which it comes into contact. Absorptive capacity can vary significantly with the nature of the liquid being absorbed and with the manner in which the liquid contacts the polymer material. For purposes of this invention, Absorptive Capacity is defined in terms of the amount of Synthetic Urine (as hereinafter defined) absorbed by any given polymer material in terms of grams of Synthetic Urine per gram of polymer material in a procedure hereinafter defined in the Test Methods section. Preferred crosslinked polyelectrolyte of the present invention are those which have an Absorptive Capacity of at least about 20 grams, more preferably at least about 25 grams, of Synthetic Urine per gram of polymer material. Typically, the polymer materials of the crosslinked polyelectrolyte herein have an Absorptive Capacity of from about 20 grams to about 70 grams of Synthetic Urine per gram of polymer material.

While all of the crosslinked polyelectrolyte are preferably formed from the same polymer material with the same properties, this need not be the case. For example, some crosslinked polyelectrolyte can comprise a starch-acrylic acid graft copolymer while other crosslinked polyelectrolyte can comprise a slightly network crosslinked polymer of partially neutralized polyacrylic acid. Further, the crosslinked polyelectrolyte can vary in size, shape, absorptive capacity, or any other property or characteristic. In a preferred embodiment of the present invention, the crosslinked polyelectrolyte consist essentially of slightly network crosslinked polymers of partially neutralized polyacrylic acid, each crossliked polyelectrolyte having similar properties.

PROCESS FOR MAKING POROUS ABSORBENT MATERIALS OF THE INVENTION

The present invention also involves a method for producing an absorbent material having modified surfaces, as described herein above, comprising the steps of (a) applying a first surface modification compound onto a portion of a surface of a water-insoluble, water swellable absorbent polymer, wherein the first surface modification compound has a function for modifying surface characteristics of the absorbent polymer; (b) swelling the absorbent polymer by absorbing water; and (c) removing a portion of said water while maintaining the absorbent polymer in substantially the swollen state, thereby forming a porous structure in the absorbent material. Preferably, substantially all free water (that is, water which is not bound chemically with the absorbent polymer) is removed in step (c), thereby leaving the porous structure substantially dry to the touch. Free water can include water which is retained within the passageways of the absorbent material prior to said removal step.

The portion of water removed from the swollen absorbent polymer can be removed by any means which results in the stable, porous structure. Such means can include methods that are well known in the art for the removal of water from solid or semi-solid materials.

One method of removal of the water is to extract away the moisture using an extraction solvent which is substantially miscible with water, which will not readily absorb or solubilize the surface modifying agent, which is easily removed from the swollen absorbent polymer by evaporation (i.e., has a low boiling temperature), and/or which does not have affinity or substantial reactivity for the absorbent polymer material.

A more preferred process is to use high temperature, high mass transfer means, such as high velocity air or gases, or low ambient pressures (such as partial or total vacuums), or any combination of these, to remove such water directly from the swollen absorbent polymer. Such process is preferred because the water is removed without the need to introduce other chemicals or solvents to extract the water. Most preferably, a process will remove the free water very quickly before the drying particle, and the open passageways therein, have an opportunity to collapse.

Rapid removal of the water from typical hydrogel absorbent polymer materials, without collapse of the passageways requires special processing conditions. Without being bound by any theory, it is believed that the collapse of the particle, more specifically the collapse of inter-particle passageways in the absorbent polymer, occurs due to the high capillary retention of water in such passageways as such water is being removed. Removal of water from the passageway draws the passageway inward due to the high capillary forces associated with the attraction of the water to the polymer surfaces. As the last amounts of free water are removed from the capillary or passage, the surfaces of the polymer, which include carboxyl and hydroxyl groups, can become chemically bonded together; this process is commonly referred to as "hydrogen bonding". This phenomenon is commonly encountered in the drying water from cellulosic fibers and cellulosic structures having small capillaries and/or fiber diameters. The effect of hydrogen bonding can be demonstrated by tissue or towel paper, wadding the paper into a ball, and allowing the paper to dry. Upon drying, usually taking several days, or by using forced heat drying, the dried paper becomes a tight, hardened inflexible structure.

Therefore, special drying processes for rapidly removing water from typical hydrogel absorbent polymer materials, without collapse of the passageways, is required. Such processes can include, but are not necessarily limited to: vacuum flash drying; high temperature, counter-current or co-current air drying; fluid bed drying; dielectric or infrared drying; freeze drying; and combinations thereof. Such processes are described in the following references, the disclosures of which are incorporated by reference: Handbook of Industrial Drying, Marcel Dekker Inc. (Arun S. Mujumdar, Ed.), 1987 (ISBN 0-8247-7606-2); Flash Drying, Bilgin Kisakurek (pp. 475–499); Microwave and Dielectric Drying, Robert F. Schiffmann (pp. 327–356); Freeze Drying, Athanasios Liapis (pp. 295–326); and *Application of infrared radiation for dying or particulate materials*, Jakobsen & Driscoll (pp. 704–711), Drying '92 (Arun S. Mujumdar, Ed.), Elsevier Sci. Publ. (ISBN 0-444-89393-8).

It is usually sufficient to remove enough of the free water, rapidly and without substantial collapse, by such process that minor amounts of moisture can then be removed without further collapse by conventional drying methods, include air drying, fluid bed drying, and the like.

In further preferred embodiments, the method of producing the absorbent material having modified surface characteristics comprises the steps of (a) applying a first surface modification compound onto a portion of a surface of a water-insoluble, water-swellable absorbent polymer, wherein the first surface modification compound has a function for modifying surface characteristics of the absorbent polymer; (b) swelling the absorbent polymer by absorbing water; (c1) freezing the swollen absorbent polymer and; (c2) removing a portion of water from the frozen swollen absorbent polymer, thereby forming a porous structure in the absorbent material.

In preferred embodiments, the absorbent polymer material as a precursor can have a number of shapes and sizes. For example, such precursor absorbent polymer material can be typically in the form of particles, sheets, films, cylinders, blocks, fibers, filaments, or other shaped elements. Preferably, discrete units, more preferably precursor particles of the absorbent polymer are used. In an alternate preferred embodiment, an absorbent macrostructure or sheet comprising a multiplicity of interconnected absorbent particles of the absorbent polymer can be used as the precursor.

In preferred embodiments, a variety of reagents for modifying surface characteristics of absorbent polymer materials can be used for the first surface modification compound. Preferably, such reagents include chemical compounds for improving distribution and dispersion of liquids in absorbent polymer materials.

In more preferred embodiments, one of the above described polyethers including non-reactive polyethers and reactive polyethers can be used as the first surface modification compound. Such polyethers can be applied by any of various techniques and apparatus used for applying materials to the other materials including coating, dumping, dropping, condensing, spraying, or immersing the reactive polyether onto the absorbent polymer material. As used herein, the term "applied onto" means that the reactive polyether will be on at least a portion of the surface area of the absorbent polymer material. Preferably, the reactive polyether is applied onto all of the surface of the absorbent polymer material.

In a preferred embodiment, the polyether is combined with the absorbent polymer, and the two components are mixed, preferably thoroughly mixed, using any of a number of mixing techniques and apparatus, including various mixers, sprayers, or kneaders, as are known in the art. Therefore, in an embodiment one of the reactive polyether is bonded to the surface of the absorbent polymer through a covalent bond, in another embodiment another one of the reactive polyether is bonded to the surface of the absorbent polymer via an electrostatic interaction, and yet another embodiment one of the non-reactive polyether is bonded to the surface of the absorbent polymer via intermolecular interactions, as herein before described.

In another alternate preferred embodiment, one of the above described polycations can be used as the first surface modification compound.

In a preferred embodiment, the step of (a) is carried out before the step of (b) so that the first surface modification compound bonds to at least a portion of the surface of the absorbent polymer before swelling of the absorbent polymer. The absorbent polymer swells by application of water. The amount of the applied water is to be at least sufficient to cause the absorbent polymer to swell by absorbing the water. Preferably, the ratio of the water to the absorbent polymer will be in the range of from about 1:1 to about 50:1, more preferably from about 3:1 to about 20:1.

In a preferred embodiment, the first surface modification compound (i.e. a polyether or a polycation) is dissolved into water to make an aqueous liquid mixture comprising the water and the first surface modification compound. The first surface modification compound can be dissolved in the water by any of various techniques and apparatus used for dissolving materials to solutions known in the art. The aqueous liquid mixture can contain an additional solvent and/or further material, that adversely effect absorbency or the liquid wettability of the absorbent polymer. For example, the low molecular weight alcohols such as methanol, ethanol, propanol, or acetone can be contained in the liquid mixture as well as the first surface modification compound. After preparing the aqueous liquid mixture, the aqueous liquid mixture is applied onto the absorbent polymer.

The aqueous liquid mixture can be applied onto the absorbent polymer. The aqueous liquid mixture can be applied by any of various techniques and apparatus used for applying solutions to materials including coating, dumping, pouring, dropping, spraying, atomizing, condensing, or immersing the aqueous liquid mixture onto the absorbent polymer. Thus, the aqueous liquid mixture can be applied onto only some of the absorbent polymer, onto all of the absorbent polymer, onto only a portion of some or all of the absorbent polymer.

In some preferred embodiments, the first surface modification compound (i.e. a polyether or a polycation) is dissolved into an organic solvent to make an organic solution. The first surface modification compound can be dissolved in the organic solvent by any of various techniques and apparatus used for dissolving materials to solutions known in the art. The organic solution is applied onto the portion of the surface of the absorbent polymer.

In an alternative preferred embodiment, the step of (a) is carried out after the step of (b). More specifically, water or other aqueous solution is first applied onto a non-swollen absorbent polymer. After the swelling of the absorbent polymer, the first surface modification compound is applied onto the swollen absorbent polymer whereby the first surface modification compound bonds to the surface of the swollen absorbent polymer.

Upon contacting with the aqueous liquid mixture or water, the absorbent polymer starts to swell by absorbing water. Substantially, most of the swelling of the porous absorbent material is conducted during and/or after applying the aqueous liquid mixture or the water onto the absorbent polymer. In preferred embodiments, more than about 60%, more preferably more than about 80%, most preferably more than about 95% of the applied water is to be absorbed by the swelling of the absorbent polymer. The actual temperature used for the swelling will vary depending upon the specific polymer materials used herein. Preferred swelling conditions will involve a temperature of from about −5° C. to 60° C. More preferably, the swelling is carried out at a temperature from about −2° C. to 30° C., most preferably from about 0° C. to 10° C.

In a preferred embodiment where the reactive polyether is mixed with a solvent such as an organic solvent or an aqueous mixture solvent, the reactive polyether is caused to react with the absorbent polymer. In an embodiment where the reactive polyether includes a plurality of cationic groups for maling the ionic bond, the reaction can be carried out at room temperature, whereas in another embodiment a higher temperature will be required to cause the chemical bonding. For example, in an embodiment where the reactive polyether includes a halogen terminal group or a epoxy terminal group for making the covalent bond, heating of the aqueous liquid mixture and the absorbent polymer is required to cause effective chemical bonding. Preferably, the temperature of the aqueous liquid mixture and the absorbent polymer is maintained in the range of from about 60° C. to about 250° C., more preferably from about 80° C. to about 200° C. In some embodiments, a catalyst such as Lewis base is preferably used for promoting the reaction between the reactive polyether and the absorbent polymer.

In alternative preferred embodiments, the swollen water-insoluble, water-swellable absorbent polymer can be made directly from polymerizable, unsaturated, acid-containing monomers using an aqueous solution polymerization method as described in the WATER-INSOLUBLE WATER-SWELLABLE POLYMER MATERIALS section. Such swollen absorbent polymer is also used for making porous absorbent materials of the present invention.

After making the swollen absorbent polymer, the swollen absorbent polymer is frozen; for example, by applying a refrigeration means. The freezing of the swollen absorbent polymer can be made by any of various techniques and apparatus used for freezing materials. For example, the swollen absorbent polymer is carried or passed into an externally refrigerated compartment and retained therein until frozen. Alternatively, the swollen absorbent polymer can be circulated around a source of refrigeration such as cooling tubes or a bath containing coolant, e.g., liquid nitrogen, dry ice, alcohol solution, or the like and the frozen slurry collected.

In preferred embodiments, the freezing of the swollen absorbent polymer is effected by cooling at temperature below about −10° C., more preferably below about −30° C., for a sufficient time to cause the freezing. If the temperature is too high or the time is too short, the swollen absorbent polymer will not be completely frozen. Typically, more than about 60%, preferably more than about 80%, more preferably more than about 95%, most preferably all by weight of the swollen absorbent polymer is to be frozen.

After the freezing of the swollen absorbent polymer, the portion of the frozen water contained in the frozen absorbent polymer is removed or dried by applying a drying means without passing through the liquid state, i.e. the ice is converted into the gaseous state by maintaining the absorbent polymer below the ice's melting temperature. In other words, the resulting ice in the frozen absorbent polymer is sublimed and the water vapor is carried away leaving a substantially water-free material. The sublimation of ice is accomplished generally by subjecting the frozen swollen absorbent polymer to a low pressure environment. In preferred embodiments, in order to effect effective rates of sublimation and removal of water to the vapor phase, the frozen absorbent polymer is subjected to a subatmospheric pressure environment under which conditions water sublimates directly from the solid phase to the vapor phase. Vacuum means for providing such a subatmospheric pressure environment are well known in the art of freeze drying. Typically such subatmospheric pressure is less than about 5.0 Torr and preferably, less than about 1 Torr. In preferred embodiments, more than about 80%, more preferably more than about 90%, most preferably more than about 97% by weight of the water or ice contained in the frozen absorbent polymer is to be removed.

In a most preferred embodiment, the step of (c2) is carried out by drying the frozen swollen absorbent polymer while maintaining the frozen state of the frozen absorbent polymer. Therefore, preferably the drying step of the frozen swollen absorbent polymer is conducted in the same apparatus used for the refrigeration means.

It should be noted that in some embodiments the swollen absorbent polymer can be directly subjected to a subatmospheric pressure environment without the prefreezing. Because of the latent heat of evaporation/sublimation, the swollen absorbent polymer can become frozen spontaneously.

In a further preferred embodiment, the step of (a) is carried out after the step of (c2). More specifically, after making an absorbent polymer material having a porous structure, the first surface modification compound is applied onto the porous absorbent polymer material whereby the first surface modification compound bonds to the surface of the porous absorbent polymer material.

In a further preferred embodiment, the method further comprises the step of (e) applying a second surface modification compound onto a portion of a surface of the absorbent polymer thereby bonding the second surface modification compound to the absorbent polymer. The second surface modification compound has an additional function for modifing surface characteristics of the absorbent polymer. The additional function can be the same function that is provided by the first surface modification compound. Thus, the same compound as the first surface modification compound can be also used as the second surface modification compound. Therefore, in a preferred embodiment, one of the above described polyethers including non-reactive polyethers and reactive polyethers can be used as the second surface modification compound. In another alternate preferred embodiment, one of the above described polycations can be used as the second surface modification compound thereby bonding the second surface modification compound to the absorbent polymer via the electrostatic interaction. In a more preferred embodiment, the first surface modification compound is one of a polyether and a polycation, while the second surface modification compound is the other one of the polyether and the polycation.

In a preferred embodiment, the step of (e) is carried out before the step of (b). More specifically, after the application of the first surface modification compound onto the absorbent polymer, the second surface modification compound is further applied onto the absorbent polymer. Thus, the second surface modification compound also bonds to the surface of the absorbent polymer before swelling of the absorbent polymer.

In an alternative preferred embodiment, the step of (e) is carried out after the step of (b). More specifically, water is first applied onto a non-swollen absorbent polymer. After the swelling of the absorbent polymer, the second surface modification compound is applied onto the swollen absorbent polymer whereby the second surface modification compound bonds to the surface of the swollen absorbent polymer.

In a further alternative preferred embodiment, the step of (e) is carried out after the step of (c2). More specifically, after making an absorbent polymer material having a porous structure, the second surface modification compound is applied onto the porous absorbent polymer material whereby the second surface modification compound bonds to the surface of the porous absorbent polymer material.

In still further preferred embodiments, the method of producing the absorbent material having modified surface characteristics comprises the steps of (A) making a porous absorbent polymer; and (B) applying a first surface modification compound onto a surface of the porous absorbent polymer, wherein the first surface modification compound has a function for modifying surface characteristics of the porous absorbent polymer.

In a preferred embodiment, the step (A) for malting a porous absorbent polymer comprises the steps of, (1) forming a reaction mixture comprising (i) a substantially water-soluble unsaturated monomer comprising neutralized carboxyl groups, (ii) a substantially water-soluble internal crosslinking agent capable of reacting with the monomer to form a absorbent polymer material; and (iii) a substantially water-soluble solvent, (2) dispersing a substantially water-insoluble blowing agent in the reaction mixture to form a dispersion of particles of the blowing agent in the reaction mixture, (3) expanding the blowing agent particles to form an expanded structure in the reaction mixture, and (4) reacting the monomer and the internal crosslinking agent to form a porous absorbent polymer.

A preferred process of the steps from (1) to (4) and an additional preferred process are described in U.S. application Ser. No. 08/038,580, to Dean V. Phan et al, entitled "Superabsorbent Polymer Foam", Case No. 4838, filed Mar. 26, 1993, the disclosure of which is incorporated by reference.

In a preferred embodiment, the step (A) for maling a porous absorbent polymer comprises the steps of; (1) forming a reaction mixture comprising (i) a substantially water-soluble unsaturated monomer comprising neutralized carboxyl groups, (ii) a substantially water-soluble internal crosslinking agent capable of reacting with the monomer to form a absorbent polymer material; and (iii) a substantially water-soluble solvent, (2) dispersing a substantially water-insoluble spacing agent in the reaction mixture to form a dispersion of particles of the spacing agent in the reaction mixture, (3) reacting the monomer and the internal crosslinking agent to form a absorbent polymer, and (4) removing the dispersion of particles of the spacing agent from the water-insoluble, water-swellable polymer to form a porous water-insoluble, water-swellable polymer.

The resulting material of the present invention is a porous absorbent material which has surprisingly improved wettability and dispersibility with liquids, particularly with urine and blood, as compared to that of conventionally derived porous absorbent material, while maintaining the substantially same absorption capacity and liquid retention. Under microscopic observations, the freeze dried absorbent material is in the form of discrete platelets, flakes, or sheets. The freeze-dried absorbent materials tend to appear as walls surrounding and defining cellular voids. Macroscopically, it is believed that this morphology results in the sponge-like or porous appearance of the freeze dried absorbent material. It is also noted that while cells are apparently surrounded by sheet-like loose polymer flakes, the sheets are to some degree discontinuous and exhibit holes and, in general, resemble a leaf-like structure.

ABSORBENT ARTICLES MADE FROM THE POROUS ABSORBENT MATERIALS

The porous absorbent materials according to the present invention can be used for many purposes in many fields of use. For example, the porous absorbent materials can be used for packing containers; drug delivery devices; wound cleaning devices; burn treatment devices; ion exchange column materials; construction materials; agricultural or horticultural materials such as seed sheets or water-retentive materials; and industrial uses such as sludge or oil dewatering agents, materials for the prevention of dew formation, desiccants, and humidity control materials.

Because of the unique absorbent properties of the porous absorbent materials of the present invention, they are especially suitable for use as absorbent cores in absorbent articles, especially disposable absorbent articles. As used herein, the term "absorbent article" refers to articles which absorb and contain body exudates and more specifically refers to articles which are placed against or in proximity to the body of the wearer to absorb and contain the various exudates discharged from the body. Additionally, "disposable" absorbent articles are those which are intended to be discarded after a single use (i.e., the original absorbent article in its whole is not intended to be laundered or otherwise restored or reused as an absorbent article, although certain materials or all of the absorbent article can be recycled, reused, or composted).

In general, an absorbent article comprises: (a) a liquid pervious topsheet which is located adjacent to the wearer's body (b) a liquid impervious backsheet which is located distant from the wearer's body and adjacent to the wearer's clothing; and (c) an absorbent core positioned between the topsheet and the backsheet. The absorbent core comprises at least one of the above described porous absorbent materials. Preferably, the absorbent core further comprises a substrate web attached to the porous absorbent material. Alternatively, the absorbent core further comprises an envelope web encasing the porous absorbent material. In more preferred embodiments, the porous absorbent material in the absorbent core has a basis weight of from about 60 $g/m^2$ to about 1500 $g/m^2$, more preferably from about 100 $g/m^2$ to about 1000 $g/m^2$, most preferably from about 150 $g/m^2$ to about 500 $g/m^2$ of the porous absorbent material.

In some preferred embodiments, the absorbent core can further comprise fibers or fluff pulp (fibrous or fiber material), more specifically, non-absorbent-gelling fibers. Such fiber material can be used as reinforcing members in the absorbent core, improving fluid handling of the core, as well as a co-absorbent with the absorbent polymers. Preferably, the absorbent core includes from about 20% to about 90% by weight of the porous absorbent material and from about 80% to about 10% by weight of such non-absorbent-gelling fiber material distributed within the porous absorbent material.

Any type of fiber material which is suitable for use in conventional absorbent products can be used in the absorbent core herein. Specific examples of such fiber material include cellulose fibers, modified cellulose fibers, rayon, polypropylene, and polyester fibers such as polyethylene terephthalate (DACRON), hydrophilic nylon (HYDROFIL), and the like. Examples of other fiber materials for use in the present invention in addition to some already discussed are hydrophilized hydrophobic fibers, such as surfactant-treated or silica-treated thermoplastic fibers derived, for example, from polyolefins such as polyethylene or polypropylene, polyacrylics, polyamides, polystyrenes, polyurethanes and the like. In fact, hydrophilized hydrophobic fibers which are in and of themselves not very absorbent and which, therefore, do not provide webs of sufficient absorbent capacity to be useful in conventional absorbent structures, are suitable for use in the absorbent core by virtue of their good wicking properties. This is because, in the absorbent core herein, the wicking propensity of the fibers is as important, if not more important, than the absorbent capacity of the fiber material itself due to the high rate of fluid uptake and lack of gel blocking properties of the absorbent core. Synthetic fibers are generally preferred for use herein as the fiber component of the absorbent core. Most preferred are polyolefin fibers, preferably polyethylene fibers.

Other cellulosic fiber materials which can be useful in certain absorbent cores herein are chemically stiffened cellulosic fibers. Preferred chemically stiffened cellulosic fibers are the stiffened, twisted, curled cellulosic fibers which can be produced by internally crosslinking cellulose fibers with a crosslinking agent. Suitable stiffened, twisted, curled cellulose fibers useful as the hydrophilic fiber material herein are described in greater detail in U.S. Pat. No. 4,888,093 (Dean et al), issued Dec. 19, 1989; U.S. Pat. No. 4,889,595 (Herron et al), issued Dec. 26, 1989; U.S. Pat. No. 4,889,596 (Schoggen et al), issued Dec. 26, 1989; U.S. Pat. No. 4,889,597 (Bourbon et al), issued Dec. 26, 1989; and U.S. Pat. No. 4,898,647 (Moore et al), issued Feb. 6, 1990, all of which are incorporated by reference.

A preferred embodiment of the disposable absorbent article is a diaper. As used herein, the term "diaper" refers to a garment generally worn by infants and incontinent persons that is worn about the lower torso of the wearer. A preferred diaper configuration for a diaper comprising an absorbent core is described generally in U.S. Pat. No. 3,860,003 (Buell), issued Jan. 14, 1975, which is incorporated by reference. Alternatively preferred configurations for disposable diapers herein are also disclosed in U.S. Pat. No. 4,808,178 (Aziz et al), issued Feb. 28, 1989; U.S. Pat. No. 4,695,278 (Lawson), issued Sep. 22, 1987; U.S. Pat. No. 4,816,025 (Foreman), issued Mar. 28, 1989; and U.S. Pat. No. 5,151,092 (Buell et al.), issued Sep. 29, 1992, all of which are incorporated by reference.

Another preferred embodiment of the disposable absorbent article is a catamenial product. Preferred catamenial products comprise a formed-film, apertured topsheet as disclosed in U.S. Pat. No. 4,285,343 (McNair), issued Aug. 25, 1981; U.S. Pat. No. 4,608,047 (Mattingly), issued Aug. 26, 1986; and U.S. Pat. No. 4,687,478 (Van Tilburg), issued Aug. 18, 1987, all of which are incorporated by reference.

Preferred catamenial products can comprise wings, side flaps, and other structures and elements, as described in co-pending, commonly-assigned U.S. application Ser. No. 984,071, to Yasuko Morita, entitled "Absorbent Article Having Elasticized Side Flaps", Attorney Docket No. JA-09RM, filed Nov. 30, 1992, incorporated herein by reference.

It should be understood, however, that the present invention is also applicable to other absorbent articles known commercially by other names, such as incontinent briefs, adult incontinent products, training pants, diaper inserts, facial tissues, paper towels, and the like.

ARTIFICIAL BLOOD PREPARATION

To prepare the specific artificial blood used in the test methods of the present invention, 3 grams of Gastric mucin is dissolved in 460 ml of phosphate buffer saline solution of pH 7.2. After heating the resulting solution at 50–80° C. for about 2.5 hours, 2.0 ml of 8% lactic acid is applied to the resulting solution. The resulting solution is mixed with an equal volume of a fresh, sterile defibrinated sheep blood, as a result, the resultant mixture is obtained as the blood used in the test methods.

TEST METHODS

A. Contact Angle Measurement

An absorbent material is caused to absorb certain amount (about 5–8%) of moisture and then is placed onto a horizontal supporting plate and compressed at 5–20 kg/cm$^2$ to form a sheet consisting of the compressed absorbent material. Upon supplying a drop of the blood onto the surface of the sheet, the contact angle defined by the blood drop and the surface of the sheet is measured simultaneously by a contact angle meter (type: CA-A, obtained from Kyowa Kaimen Kagaku Co., Ltd., Tokyo) equipped with a camera. The measurement is conducted under standard laboratory conditions at about 23° C. (73° F.).

B. Specific Surface Area Measurement

After the absorbent material is totally dried with a vacuum oven at 50° C. for 24–40 hours, the specific surface area is measured using the Brunauer-Emmet-Teller (BET) gas absorption method. This method involves absorbing a monolayer of a gas (Krypton) on a known mass of an absorbent material sample at liquid nitrogen temperature. The absorbed Krypton is then desorbed by raising the temperature of the sample (thermal desorption) and detected by a thermal conductivity detector (TCD) whose output is connected to an integrating recorder. The peak area of the desorbed Krypton is thus known. The specific equipment used for these measurements is Belsorp 36 obtained from Nippon Bel K.K. 0.5–1.5 Grams±0.005 grams of absorbent material sample is weighed into the sample cell of the apparatus. The cell containing the sample is then placed into the gas flow of the instrument. The samples are outgassed with a 30 ml/min Helium flow to remove any gases other than Helium from the sample, typically a minimum of 4 hours. After outgassing, the gas flow is changed to a specific Krypton-Helium gas mixture. The sample cell is immersed in liquid Nitrogen and allowed to reach equilibrium. An absorption curve is generated. The absorbed Krypton is then desorbed by removing the liquid Nitrogen and immersing the vial in warm tap water. The absorbed Krypton generates a desorption curve and a peak value. The specific surface area is obtained from BET plot.

C. Bulk density measurement

After the absorbent material is totally dried with a vacuum oven at 50° C. for 24 hours, the sample is packed in a 10 ml graduated cylinder. During the packing, the graduated cylinder is kept at the table without being tapped. The weight of the packed sample is measured and the bulk density is obtained by dividing the measured sample weight by the sample volume (10 ml).

D. Absorbency Time Measurement 0.25 Grams of absorbent material is placed into a Petri dish and 5 ml of the artificial blood is applied to the absorbent material. The mixture is stirred with a spatula to maintain the contact of the absorbent material with the artificial blood. The time required for the disappearance of the liquid is recorded as the absorbency time.

PRECURSOR PARTICLE EXAMPLE

An aqueous monomer solution is prepared consisting of 40 grams of partially neutralized acrylic acid having a 75 mol % portion thereof neutralized with caustic soda, 0.037 grams of N,N'-methylene-bis-acrylamide, and 60 grams of water. The aqueous monomer solution is fed into the reaction vessel, which is subsequently purged with nitrogen gas to remove the remaining entrapped air from the reaction system. Then, the mixture was stirred and heated to about 45° C., and a solution of 0.23 grams of 2,2'-azo-bis-(2-amidinopropane)-dihydrochloride in 1 grams of water is added thereto as a polymerization initiator. Polymerization begins about 15 minutes after the addition of the polymerization initiator. With the progress of the polymerization, the aqueous monomer solution gives rise to a soft water-containing gel. The inner temperature of the reaction system is kept at 80–90° C. for hours to further complete the polymerization. A swollen gel polymer is formed. This swollen gel polymer is itself used in later Examples.

The resultant swollen gel polymer thus obtained is spread on a standard #50 size metal gauge and dried with a hot air at 150° C. The dried particles are pulverized with a hammer type crusher and sifted with a standard #20 sieve (850 microns) to obtain particles that pass through the standard #20 sieve. As a result, dry white precursor particles of absorbent polymer are obtained.

EXAMPLE 1

A solution is prepared consisting of 2 grams of polyethylene glycol (molecular weight 600), 3.3 grams of Kymene Plus (30% resin active), and 1,500 grams of distilled water. The polyethylene glycol is 2 weight parts and the Kymene Plus is 1 weight part for 100 weight parts of precursor particles of the absorbent polymer. The solution is applied to 100 grams of precursor particles made in accordance with the Precursor Particle Example. The precursor particles have a particle size such that the precursor particles pass through a standard #20 sieve (850 microns) and are retained on a standard #100 sieve (150 microns). The mixture is thoroughly mixed with a stirring spatula until all of the precursor particles are contacted with the above solution. Upon contacting with the solution, the absorbent polymer starts to swell by absorbing the water included in the solution. Mixing temperature is about 2° C. The resulting swollen absorbent polymer is then freeze dried using a freezing drying apparatus (available from TOKYO RIKAK CO., LTD., Tokyo). The swollen absorbent polymer is introduced into stainless trays which are then placed in a freezer at an effective cooling temperature of about −20° C. The frozen absorbent polymer is then placed in the freeze drying apparatus and the water is removed by sublimation under a vacuum of about 0.05 Torr. The dried absorbent material is pulverized with a hammer type crusher and sifted with a standard #20 sieve (850 microns) to obtain particles that pass through the standard #20 sieve. As a result, dry white particles of the porous absorbent material are obtained. The contact angle of blood on the resultant absorbent material is less than about 10 degree. The absorbency time of the resultant absorbent material is about 6 seconds. The specific surface area of the resultant absorbent material is about 1200 $cm^2/g$. The bulk density of the resultant absorbent material is about 0.1 gram/cc.

EXAMPLE 2

An aqueous solution is prepared consisting of 2 grams of polyethylene glycol (molecular weight 600), 3.3 grams of Kymene (30% resin active), and 1,200 grams of distilled water. The polyethylene glycol is 2 weight parts and the Kymene Plus is 1 weight part for 100 weight parts of the absorbent polymer. The solution is sprayed onto the swollen gel polymer made before drying in accordance with the Precursor Particle Example and mixed together. A sprayer (type: 24-182-04; available from Iuchi Seieido Co., Ltd., of Osaka, Japan) is used. The resulting mixture is then freeze dried using the freezing drying apparatus. The mixture of absorbent polymer is introduced into stainless trays which are then placed in a freezer at an effective cooling temperature of about −20° C. The frozen absorbent polymer is then placed in the freeze drying apparatus and the water is removed by sublimation under a vacuum of about 0.05 Torr. The dried absorbent material is pulverized with a hammer type crusher and sifted with a standard #20 sieve (850 microns) to obtain particles that pass through the standard #20 sieve. As a result, dry white particles of the porous absorbent material are obtained. The contact angle of blood on the resultant absorbent material is less than about 10 degree. The absorbency time of the resultant absorbent material is about 10 seconds. The specific surface area of the resultant absorbent material is about 1500 $cm^2/g$. The bulk density of the resultant absorbent material is about 0.1 gram/cc.

EXAMPLE 3

An aqueous solution is prepared consisting of 2 grams of the reactive polyether (TEPA-$E_{15}$) and 1000 grams of distilled water. The reactive polyether was 2 weight parts for 100 weight parts of the absorbent polymer. The solution is sprayed onto 100 grams of the precursor particles made in accordance with the Precursor Particle Example and mixed together. The precursor particles absorb water from the solution and begin to swell. The resulting swollen mixture is then freeze dried using the freezing drying apparatus. The mixture of absorbent polymer is introduced into stainless trays which are then placed in a freezer at an effective cooling temperature of about −20° C. for about 5 hours. The frozen absorbent polymer is then placed in the freeze drying apparatus and substantially all the water is removed by sublimation under a vacuum of about 0.05 Torr. The dried absorbent material is pulverized with a hammer type crusher and sifted with a standard #20 sieve (850 microns) to obtain particles that pass through the standard #20 sieve. As a result, dry white particles of the porous absorbent material are obtained. The contact angle of blood on the resultant absorbent material is less than about 10 degree. The absorbency time of the resultant absorbent material is about 11 seconds. The specific surface area of the resultant absorbent material is about 1500 $cm^2/g$. The bulk density of the resultant absorbent material is about 0.1 gram/cc.

EXAMPLE 4

1,500 Grams of distilled water is applied to 100 grams of precursor particles made in accordance with the Precursor Particle Example. The precursor particles have a particle size such that the precursor particles pass through a standard #20 sieve (850 microns) and are retained on a standard #100 sieve (150 microns). The mixture is thoroughly mixed with a stirring spatula until all of the precursor particles are contacted with the above solution. Upon contacting with the solution, the absorbent polymer starts to swell by absorbing the water included in the solution. Mixing temperature is about 2° C. The resulting swollen absorbent polymer is then freeze dried using a freezing drying apparatus (available from TOKYO RIKAKIKAI CO., LTD., Tokyo). The swollen absorbent polymer is introduced into stainless trays which are then placed in a freezer at an effective cooling temperature of about −20° C. for about 5 hours. The frozen absorbent polymer is then placed in the freeze drying apparatus and substantially all the water is removed by sublimation under a vacuum of about 0.05 Torr. As a result, dry white particles of the porous absorbent material are obtained.

100 Grams of the dried porous absorbent polymer are placed in a 2 liter flask. A solution is prepared consisting of 2 grams of a polyethylene glycol (molecular weight 600), 1 gram of polyallylamine and 500 grams of methanol. The solution is introduced into the flask. The mixture is thoroughly mixed with a stirring spatula until all of the absorbent polymer particles are wetted with the above solution. After the methanol included in the resultant mixture is evaporated by a rotary evaporator, the resultant product is vacuum dried at 40° C. to obtain the absorbent material. The dried absorbent material is pulverized with a hammer type crusher and sifted with a standard #20 sieve (850 microns) to obtain particles that pass through the standard #20 sieve. As a result, dry white particles of the porous absorbent material are obtained. The contact angle of blood on the porous absorbent material is less than about 10 degree. The absorbency time is about 6 seconds. The specific surface area of the resultant absorbent material is about 1200 $cm^2/g$. The bulk density of the resultant absorbent material is about 0.1 gram/cc.

What is claimed is:

1. A porous absorbent material having walls surrounding and defining cellular voids, and having modified surface characteristics, said material comprising:
   a water-insoluble, water-swellable polymer;
   a positive-charge supplying compound bonded to the water-insoluble, water-swellable polymer; and
   a hydrophilic compound bonded to said water-insoluble, water-swellable polymer wherein said absorbent material has been freeze dried so that said material is in the form of discrete platelets, flakes or sheets when viewed microscopically, each of said platelets, flakes or sheets, having said cellular voids, and the contact angle of blood on a surface of said absorbent material is from about 0 to about 40 degree.

2. A porous absorbent material having walls surrounding and defining cellular voids, and having modified surface characteristics, said material comprising:

a water-insoluble, water-swellable polymer;

a positive-charge supplying compound bonded to the water-insoluble, water-swellable polymer; and a non-ionic hydrophilic compound bonded to said water-insoluble, water-swellable polymer;

wherein said absorbent material has been freeze dried so that said material is in the form of discrete platelets, flakes or sheets when viewed microscopically, each of said platelets, flakes or sheets, having said cellular voids, and the contact angle of blood on a surface of said absorbent material is from about 0 to about 40 degree.

3. The porous absorbent material according to claim 1 wherein said hydrophilic compound is selected from the group consisting of a positive-charge supplying compound, and a non-ionic hydrophilic compound.

4. The porous absorbent material according to claim 2 wherein said positive-charge supplying compound is a polycation having a plurality of positive-charged groups.

5. The porous absorbent material according to claim 4 wherein said polycation is selected from the group consisting of (1) polymers having primary amine groups; (2) polymers having secondary amine groups; (3) polymers having tertiary amine groups; and (4) polymers having quaternary amine groups.

6. The porous absorbent material according to claim 2 wherein said non-ionic hydrophilic compound is a polyether.

7. The porous absorbent material according to claim 6 wherein said polyether is a non-reactive polyether.

8. The porous absorbent material according to claim 6 wherein said non-ionic hydrophilic compound is a reactive polyether.

9. The porous absorbent material according to claim 7 wherein said non-reactive polyether is selected from the group consisting of a non-reactive polyethylene glycol, a non-reactive polypropylene glycol, and a non-reactive poly(oxyethylene-oxypropylene) copolymer.

10. The porous absorbent material according to claim 8 wherein said reactive polyether is selected from the group consisting of a reactive polyethylene glycol, a reactive polypropylene glycol, and a reactive poly(oxyethylene-oxypropylene) copolymer.

11. The porous absorbent material according to claim 2 wherein the porous absorbent material absorbs at least one of urine and menstrual fluid.

12. The porous absorbent material according to claim 2 wherein said porous absorbent material has a bulk density of from about 0.01 g/cc to about 0.4 g/cc.

13. The porous absorbent material according to claim 12 wherein said bulk density is from about 0.03 g/cc to about 0.35 g/cc.

14. The porous absorbent material according to claim 13 wherein said bulk density is from about 0.06 g/cc to about 0.3 g/cc.

15. The porous absorbent material according to claim 2 wherein said porous absorbent material has a specific surface area of at least about 400 $cm^2/g$.

16. The porous absorbent material according to claim 15 wherein said specific surface area is at least about 600 $cm^2/g$.

17. The porous absorbent material according to claim 16 wherein said specific surface area is at least about 1000 $cm^2/g$.

18. The porous absorbent material according to claim 2 wherein said water-insoluble, water-swellable polymer is a crosslinked polyelectrolyte.

19. The porous absorbent material according to claim 18 wherein said crosslinked polyelectrolyte is selected from the group consisting of a crosslinked polyacrylate sodium, a crosslinked polymethacrylate sodium, a crosslinked polyacrylate potassium, a crosslinked polymethacrylate potassium, a crosslinked starch grafted polyacrylate, a crosslinked starch grafted polymethacrylate, a crosslinked polyvinyl alcohol grafted polyacrylate, a crosslinked polyvinyl alcohol grafted polymethacrylate, a crosslinked carboxymethyl cellulose, a crosslinked cellulose grafted polyacrylate, and a crosslinked cellulose grafted methacrylate.

20. The porous absorbent material according to claim 2 wherein said porous absorbent material is in the form of a sheet, particle, fiber, agglomerate, block, or filament.

21. An absorbent article comprising: (a) a liquid pervious topsheet; (b) a liquid impervious backsheet; and (c) an absorbent core positioned between said topsheet and said backsheet, wherein said absorbent core comprises at least one porous absorbent material of claim 1 or 2.

22. The absorbent article of claim 21 wherein said absorbent core further comprises a substrate web attached to said porous absorbent material.

23. The absorbent article of claim 21 wherein said absorbent core further comprises an envelope web encasing said porous absorbent material.

24. The absorbent article of claim 21 wherein said porous absorbent material in said absorbent core has a basis weight of from about 60 g/m2 to about 1500 g/m2 of said porous absorbent material.

25. The absorbent article of claim 24 wherein said basis weight is from about 100 g/m2 to about 1000 g/m2 of said porous absorbent material.

26. The absorbent article of claim 25 wherein said basis weight is from about 150 g/m2 to about 500 g/m2 of said porous absorbent material.

27. The absorbent article of claim 21 wherein said absorbent core further comprises fibers distributed within said porous absorbent material.

28. The absorbent article of claim 27 wherein said absorbent core has from about 20% to about 90% by weight of said porous absorbent material.

29. The absorbent article according to claim 21 wherein said absorbent article is a catamenial product, a diaper or an adult incontinence product.

* * * * *

UNITED STATES PATENT AND TRADEMARK OFFICE
CERTIFICATE OF CORRECTION

PATENT NO.    : 5,985,432
DATED         : November 16, 1999
INVENTOR(S)   : Wang et al.

It is certified that error appears in the above-identified patent and that said Letters Patent is hereby corrected as shown below:

Column 1,
Line 34, please delete "usefull" and insert therefor -- useful --.

Column 2,
Line 42, after "polymer" please delete "," (the comma) and insert therefor --; -- ( a semi-colon).
Line 66, please delete "maling" and insert therefor -- making --.

Column 3,
Line 6, please delete "modifyng" and insert therefor -- modifying --.

Column 7,
Line 61, please delete "maling" and insert therefor -- making --.

Column 10,
Line 43, please delete "a" before "(crotonic acid)".
Line 43, please delete "a-phenylacryllic" and insert therefor -- a-phenylacrylic --.

Column 12,
Line 10, please delete "abovereferenced" and insert therefor -- above-referenced --.

Column 13,
Line 17, please delete "crossliked" and insert therefor -- crosslinked --.

Column 14,
Line 35, please delete "*dying*" and insert therefor -- *drying* --.

Column 16,
Line 40, please delete "maling" and insert therefor -- making --.

Column 17,
Line 49, please delete "prefeezing" and insert therefor -- pre-freezing --.
Line 66, please delete "fing" and insert therefor -- fying --.

Column 18,
Line 48, please delete "maling" and insert therefor -- making --.
Line 49, please delete "," (the comma) before "(1)" and insert therefor --; -- (a semi-colon).

UNITED STATES PATENT AND TRADEMARK OFFICE
CERTIFICATE OF CORRECTION

PATENT NO. : 5,985,432
DATED : November 16, 1999
INVENTOR(S) : Wang et al.

It is certified that error appears in the above-identified patent and that said Letters Patent is hereby corrected as shown below:

Column 19,
Line 1, please delete "maling" and insert therefor -- making --.
Line 63, after "body" please insert -- ; -- (a semi-colon).

Column 23,
Line 9, please delete "RIKAK" and insert therefor -- RIKAKIKAI --.

Signed and Sealed this

Twenty-seventh Day of July, 2004

JON W. DUDAS
*Acting Director of the United States Patent and Trademark Office*